US008435766B2

(12) United States Patent
Kellens et al.

(10) Patent No.: US 8,435,766 B2
(45) Date of Patent: May 7, 2013

(54) ENZYMATIC OIL RECUPERATION PROCESS (75) Inventors: Marc Kellens, Mechelen-Muizen (BE); Wim De Greyt, Sinaai (BE)

(73) Assignee: N.V. Desmet Ballestra Engineering S.A., Zaventem (BE)

( * ) Notice: Subject to any disclaimer, the term of this patent is extended or adjusted under 35 U.S.C. 154(b) by 527 days.

(21) Appl. No.: 12/661,429

(22) Filed: Mar. 17, 2010

(65) Prior Publication Data

US 2010/0240917 A1    Sep. 23, 2010

Related U.S. Application Data (60) Provisional application No. 61/161,645, filed on Mar. 19, 2009.

(30) Foreign Application Priority Data

Mar. 20, 2009  (GB) .................................. 0904787.9

(51) Int. Cl.
C12P 7/64 (2006.01)
C07C 59/00 (2006.01)

(52) U.S. Cl.
USPC .......................................... 435/134; 554/213

(58) Field of Classification Search .................. 435/134; 554/213
See application file for complete search history.

(56) References Cited

U.S. PATENT DOCUMENTS

| | | | |
|---|---|---|---|
| 2,678,327 A | 5/1954 | Clayton | |
| 4,049,686 A | 9/1977 | Ringers et al. | |
| 4,927,544 A | 5/1990 | van Optstal et al. | |
| 5,264,367 A | 11/1993 | Aalrust et al. | |
| 5,532,163 A | 7/1996 | Yagi et al. | |
| 5,558,781 A | 9/1996 | Buchold et al. | |
| 6,001,640 A | 12/1999 | Loeffler et al. | |
| 6,103,505 A | 8/2000 | Clausen et al. | |
| 7,226,771 B2 | 6/2007 | Gramatikova et al. | |
| 7,494,676 B2 | 2/2009 | Chakrabarti et al. | |
| 2009/0053191 A1 | 2/2009 | Gramatikova et al. | |

FOREIGN PATENT DOCUMENTS

| | | |
|---|---|---|
| EP | 1624047 | 2/2006 |
| EP | 1624047 A1 * | 2/2006 |
| EP | 2 053 118 | 4/2009 |
| IL | 60835 | 8/1980 |

(Continued)

*Primary Examiner* — Deborah D Carr
(74) *Attorney, Agent, or Firm* — Wegman, Hessler & Vanderburg (57) ABSTRACT

A process for the recuperation of acylglycerols or acylglycerols containing free fatty acids from gums, present as aqueous emulsions, said gums being obtained by subjecting triglyceride oil to one or more degumming processes, said recuperation process comprising the steps of: subjecting said gums to enzymatic hydrolysis catalyzed by one or more enzymes with phospholipase activity; allowing said gums to separate into two or more phases, said two or more phases including at least an oily phase and an aqueous phase; and recuperating said oily phase comprising acylglycerols or acylglycerols containing free fatty acids; wherein said enzymatic hydrolysis is accelerated by adding at least part of the one or more enzymes with phospholipase activity to at least part of the water used in the recuperation and/or at least one degumming process; and/or at least part of said triglyceride oils treated in said degumming process; and/or by facilitating mixing at least part of said one or more enzymes with phospholipase activity into said gums by increasing the triglyceride oil content of said gums; and an oil obtained by this process.

9 Claims, 3 Drawing Sheets

FOREIGN PATENT DOCUMENTS

| | | |
|---|---|---|
| WO | WO95/00609 | 1/1995 |
| WO | WO2007/059927 | 5/2007 |
| WO | WO2008/036863 | 3/2008 |
| WO | WO2008094847 | 8/2008 |

* cited by examiner

ENZYMATIC OIL RECUPERATION PROCESS

CLAIM OF PRIORITY

Applicant hereby claims priority under 35 USC §119 of U.S. Provisional Patent Application Ser. No. 61/161,645 filed Mar. 19, 2009 and British Patent Application No. 0904787.9 filed Mar. 20, 2009.

FIELD OF THE INVENTION

The invention relates to an improved process for the recuperation of acylglycerols from gums obtained by degumming triglyceride oils by subjecting said gums to a hydrolysis that is catalysed by one or more enzymes with phospholipase activity.

BACKGROUND OF THE INVENTION

Edible oils as obtained by expelling and/or solvent extraction often require extensive purification. Accordingly, mucilaginous matter is removed during a degumming step, and free fatty acids are removed during the chemical neutralisation step by reacting them with caustic soda under formation of soaps. Colouring compounds are removed during the bleaching step when oil is treated with an adsorbent such as bleaching earth, and malodorous compounds are removed during the deodorisation step. This latter step can also serve the purpose of removing free fatty acids and is then commonly referred to as the steam refining or physical refining step.

Several degumming processes have been developed. The simplest process is a water degumming process, which only removes hydratable phospholipids present in the crude oil. The water degumming process does not remove non-hydratable phospholipids, which consist of calcium and magnesium salts of phosphatidic acid. To remove the latter, several processes have been developed such as the acid degumming process disclosed in U.S. Pat. No. 4,049,686, the acid refining process disclosed in Israeli patent 60835, the SOFT degumming process employing ethylene diamine tetra acetic acid (EDTA) disclosed in WO 95/00609 and various enzymatic processes.

The oldest of these enzymatic degumming processes is disclosed in U.S. Pat. No. 5,264,367. According to this patent, triglyceride oil having a phosphorus content of 50 to 250 ppm, and which is therefore likely to have been water degummed, is treated at a pH of 4 to 6 with an aqueous solution of a phospholipase A1, phospholipase A2 or phospholipase B until the phosphorus content of the oil has been reduced to less than 5 ppm. The degumming process disclosed in U.S. Pat. No. 5,558,781 also employs phospholipase enzymes with A1, A2 or B activity and also uses a separation promoter. Another process is disclosed in U.S. Pat. No. 5,532,163 in which the amount of water used to dissolve the phospholipase, which can be a phospholipase A2, and to disperse the oil into fine droplets with an average size of 0.1 to 50µ is at least 30% by weight of the oil. The use of phospholipase from *Aspergillus* is disclosed in U.S. Pat. No. 6,001,640 whereby it is stated that this enzyme has both phospholipase A1 and phospholipase A2 activity. In U.S. Pat. No. 6,103,505 an isolated peptide is disclosed that exhibits phospholipase A activity; a method for hydrolysing fatty acid groups in phospholipids or lysophospholipids by treating said phospholipids with said polypeptide is also disclosed. Finally, a process to prepare an oil that is amenable to physical refining employing an enzyme with phospholipase A1 activity has been disclosed in US 2004/0005399. However, the above degumming processes have in common that they use enzymes that hydrolyse a fatty acid glycerol bond. Consequently, they catalyse the production of free fatty acids. During the degumming process, these free fatty acids will be concentrated in the oil being degummed from which they have to be removed as part of the refining process.

A phospholipase enzyme, which is known as phospholipase C, does not cause the formation of free fatty acids because this enzyme catalyses the hydrolysis of the bond between the acylglycerol and the phosphate group. Accordingly, it liberates diacylglycerols and compounds like choline phosphate from phospholipids and monoacylglycerols and phosphates from lysophospholipids.

Such phospholipases have been disclosed in U.S. Pat. No. 7,226,771, which document also mentions that these phospholipases can be used in degumming processes of crude oil containing some phospholipids by mixing the compound with the oil to be degummed in the presence of an amount of water of 0.5 to 5%. Finally, WO 2008/094847 discloses a method for degumming an oil composition comprising the steps of (a) providing an oil composition containing a quantity of phospholipids, (b) contacting said oil composition simultaneously with one or more phospholipase A enzymes and one or more phospholipase C enzymes, under conditions sufficient for the enzymes to react with the phospholipids to create phospholipid reaction products, and (c) separating the phospholipid reaction products from the oil composition, the remaining oil composition after the separation being a degummed oil composition whereby during the step (b) the reaction of one or more phospholipase A enzymes proceeds at a faster rate than it would in the absence of said one or more phospholipase C enzymes.

The above prior art patents all aim at degumming: treating an oil containing phospholipids in such a way that the phospholipids are removed from the oil so that a degummed oil with a low residual phospholipids content results. They do this by using enzymes to hydrolyse the phospholipids. This hydrolytic activity is also used in a different process that aims at the recuperation of glyceride oil contained in the gums resulting from degumming processes of triglyceride oils.

Such oil recuperation has also been disclosed in U.S. Pat. No. 2,678,327, which describes the admixing of a liquefied, normally gaseous hydrocarbon such as propane with the hydrated gums and maintaining the resulting mixture under sufficient pressure to retain said hydrocarbon in liquid form, bringing said mixture to a temperature producing a solvent phase containing said liquefied hydrocarbon and said oil and an aqueous phase containing said gums while said gums contain sufficient water to produce a liquid aqueous phase, separating said phases, recovering de-oiled gums from said aqueous phase and vaporising said hydrocarbon from said solvent phase to recover oil therefrom. However, the use of a normally gaseous hydrocarbon such as propane necessitates the installation to be explosion proof, which requires a considerable additional investment. Moreover, the liquefaction and evaporation of this hydrocarbon require energy and thus augment the operating cost of this recovery process. It is therefore doubtful if the savings resulting from the sale of the recuperated oil as crude oil will be large enough to cover these costs.

Accordingly, a process obviating the use of organic solvents has been disclosed in EP 1 624 046. It comprises the steps of (a) providing wet gums by water degumming a crude vegetable oil, (b) mixing said wet gums with water containing a phospholipidolytic agent, (c) allowing the mixture to separate into two or more phases, said two or more phase including at least an oily phase and an aqueous phase, and (d) recuperating said oily phase. The phospholipidolytic agents comprise acids and phospholipase enzymes.

When enzymes such as phospholipase A1, A2 or B are used in the process disclosed in EP 1 624 046, the phospholipids present in the gums liberate free fatty acids. Since these acids are oil-soluble they are recuperated as part of the oily phase. When this oily phase is subsequently refined, said free fatty acids are removed from the oily phase and although they can be sold as acid oil or fatty acid distillate and can be used in oleochemical applications or as raw material for the production of biodiesel, their value will be less than that of a refined triglyceride oil. Enzymes with a phospholipase C activity do not have this disadvantage. They liberate oil-soluble diacylglycerols and water-soluble phosphates and during subsequent refining of the oily phase, the diacylglycerols are not removed from the oil. Accordingly they can be sold at full refined oil value.

Accordingly, the use of enzymes with phospholipase C activity offers advantages over the use of enzymes with phospholipase A1, A2 or B activity but in practice, the enzymes with phospholipase C activity that are commercially available are membrane-bound and have the disadvantage that they are very difficult to disperse in the gums from which the oil has to be recuperated. Consequently, the oil recuperation process as disclosed in EP 1 624 046 can be slow and unpredictable when phospholipase C is used. This process is therefore in need of improvement with respect to speed and robustness.

Another disadvantage of enzymes with phospholipase C activity is their selective activity on hydratable phospholipids. Indeed, enzymes with phospholipase C activity are only able to catalyse the hydrolysis of hydratable phospholipids whereas enzymes with phospholipase A1, A2 or B activity are able to catalyse the hydrolysis of both non-hydratable and hydratable phospholipids. Therefore, in practice, the oil recuperation process as disclosed in EP 1 624 046 leads to the recovery of an oily layer that is enriched in free fatty acids (FFA) if enzymes with phospholipase A1, A2 or B activity are used or in diacylglycerols if enzymes with phospholipase C activity are used.

OBJECT OF THE INVENTION

It is therefore an object of the invention to provide means to facilitate and improve the dispersion of enzymes with phospholipase activity in gums as obtained by degumming crude triglyceride oils.

SUMMARY OF THE INVENTION

It has surprisingly been found that the above object can be realized by an improved process for the recuperation (recovery) of acylglycerols or acylglycerols containing free fatty acids from gums that result from one or more degumming processes of triglyceride oils by subjecting said gums, present as aqueous emulsions, to an enzymatic hydrolysis that is catalysed by one or more enzymes with phospholipase activity, allowing said gums to separate into two or more phases, said two or more phases including at least an oily phase and an aqueous phase and recuperating said oily phase comprising the acylglycerols or acyl glycerols containing free fatty acids, the improvement being an acceleration of said hydrolysis realised by adding the at least part of one or more enzymes with phospholipase activity to at least part of the water used in the recuperation process and/or at least one of said degumming processes; and/or at least part of said triglyceride oils treated in said degumming process; and/or by facilitating mixing the at least part of one or more enzymes with phospholipase activity into said gums by increasing the triglyceride oil content of said gums. The accelerated hydrolysis is believed to be due to an improved dispersion of the one or more enzymes with phospholipase activity.

Aspects of the present invention are realized by a process for the recuperation of acylglycerols or acylglycerols containing free fatty acids from gums, present as aqueous emulsions, said gums being obtained by subjecting triglyceride oil to one or more degumming processes, said recuperation process comprising the steps of: subjecting said gums to enzymatic hydrolysis catalysed by one or more enzymes with phospholipase activity; allowing said gums to separate into two or more phases, said two or more phases including at least an oily phase and an aqueous phase; and recuperating said oily phase comprising acylglycerols or acylglycerols containing free fatty acids; wherein said enzymatic hydrolysis is accelerated by adding at least part of the one or more enzymes with phospholipase activity to at least part of the water used in the recuperation and/or at least one degumming process; and/or at least part of said triglyceride oils treated in said degumming process; and/or by facilitating mixing at least part of said one or more enzymes with phospholipase activity into said gums by increasing the triglyceride oil content of said gums.

Aspects of the present invention are also provided by an oil obtained by the above-described process.

Another embodiment of the present invention provides an improved process for the recuperation of acylglycerols or acylglycerols containing free fatty acids from gums that result from one or more degumming processes of triglyceride oils by subjecting said gums to an enzymatic hydrolysis that is catalysed by one or more enzymes with phospholipase activity, allowing said gums to separate into two or more phases, said two or more phases including at least an oily phase and an aqueous phase and recuperating said oily phase, the improvement being an acceleration of said hydrolysis resulting from an improved dispersion of said enzymes that is realised by adding at least part of the one or more enzymes with phospholipase activity to at least part of the water used and/or at least part of said triglyceride oils treated in said degumming process and/or by facilitating mixing at least part of the one or more enzymes with phospholipase activity into said gums by increasing the triglyceride oil content of said gums.

DETAILED DESCRIPTION OF THE INVENTION

The improved process according to the invention is particularly useful for oil mills that have to degum the crude oil they produce to ensure that it meets a sale specification and/or to prevent that the crude oil throws a deposit during transport or storage and that do not dry the ensuing gums to produce lecithin. Such oil mills normally dispose of the gums by incorporating them into the oilseed meal. However, since the pecuniary value per kilogram of meal is always lower than that of oil, there is a benefit in recuperating the oil from the gums and thereby selling less meal and more oil. In addition, the use of enzymes with phospholipase C activity causes the phospholipids to form diacylglycerols, which remain in the oily phase and are not removed during subsequent refining processes as opposed to the free fatty acids formed when phospholipases with A1, A2 or B activity are used. Therefore the oil recuperated by the process according to the invention has a high diacylglycerol content if the gums are hydrolysed by using one or more enzymes with phospholipase C activity, which may merit an increased selling price in its own right.

Gums containing triglyceride oil that is to be recuperated by the process according to the invention can originate from various vegetable oils such as soya bean oil, rapeseed oil, sunflower seed oil and the like. They can also originate from different processes such as but not limited to the water degumming process, the acid degumming process and the acid refining process. Amongst these degumming processes, the water degumming process is especially amenable to the embodiments of the invention in which at least a part of the one or more enzymes with phospholipase activity, particularly phospholipase C activity are added to at least a part of the water used in the water of the degumming process itself and/or to at least a part of the oil that is degummed.

In one embodiment of the process according to the present invention, crude oil is first of all degummed with water containing one or more enzymes with for instance phospholipase C activity, thereby providing water degummed oil and gums containing an appreciable amount of triglyceride oil and said one or more enzymes with phospholipase C activity finely dispersed in said gums. These gums are then allowed to separate into two or more phases including an oily phase, which is subsequently recuperated. Preferably, the water phase is also recuperated and used partially but preferably in its entirety in a subsequent water degumming step because this recycling utilizes residual enzyme activity and reduces the amount of fresh enzyme to be added to the water used in the water degumming step and/or to the gums, which addition also falls within the scope of the invention, and thus constitutes a saving. The total amount of water to be used in this water degumming step is usually about the same as the amount of mucilaginous matter to be removed from the crude oil by the water degumming process. Accordingly, the wet gums provided by the water degumming process generally have a water content in the range of 30 to 60% by weight but the process according to the invention is in no way limited to this range.

The total amount of water to be used in this water degumming step is usually about the same as the amount of mucilaginous matter to be removed from the crude oil by the water degumming process. Accordingly, the wet gums provided by the water degumming process generally have a water content in the range of 30 to 60% by weight but the process according to the invention is in no way limited to this range.

Whereas the standard water degumming process is carried out at a temperature of about 100° C., the water degumming process in the above embodiment of the process according to the invention has to be carried out at a lower temperature to prevent or at least minimize the thermal inactivation of the enzymes. The exact temperature limit depends on the particular enzymes used but in general, the temperature should not exceed 80° C. or even 60° C. Alternatively, at least part of the fresh enzymes can be added to the oil being water degummed before, during and/or at the end of the degumming process. This procedure also ensures proper dispersion of the enzymes through the gums and minimises their inactivation. These alternative methods of addition of at least a part of the enzymes with phospholipase activity are not incompatible with the inclusion of at least a part of the enzymes with phospholipase activity into the water used for the water degumming of crude oil.

The fresh enzymes with phospholipase C activity used in the process according to the invention preferably display a wide specificity spectrum so that most and preferably all phospholipids species present in the gums are hydrolysed. However, the use of enzymes or enzymes mixtures that do not catalyse the hydrolysis of all phospholipids species also falls within the scope of the invention.

The period of time needed for the hydration of the gums is normally some 15 minutes. During this period of time, some hydrolysis of at least some phospholipids may already take place, but since the amount of enzyme present is an order of magnitude lower than the amount required to degum the oil to a residual phosphorus content below 10 ppm in accordance with the process disclosed in U.S. Pat. No. 7,226,771, the extent of this hydrolysis will be marginal.

In general, the amount of enzyme is about 50 to 2000 ppm, preferably 100 to 500 ppm calculated on the dry gums and since the amount of water chosen normally equals the amount of mucilaginous matter this means that the amount of enzyme also corresponds to some 50 to 2000 ppm, preferably 100 to 500 ppm calculated on the water used for the water degumming itself. However, values outside this range also fall within the scope of the invention.

At this stage of the process, some water may be added to the gums to facilitate subsequent phase separation but if the aqueous phase is to be used in a subsequent water degumming process, the amount of water added to the gums should be as little as possible because the system does not have a purge for this additional water.

The process of oil exudation is quite similar to that observed in the oil recuperation process disclosed in EP 1 624 047. In the beginning little seems to happen but after a while, an oily top layer is formed that once formed, grows quite rapidly until its rate of formation decreases again. This oily top layer is then separated from the aqueous layer and other layers if present; this separation is preferably carried out mechanically by using a decanter or a centrifugal separator. Since the oil temperature is lower than the temperature used during for instance normal oil degumming or neutralization processes, the oil is more viscous. This causes the capacity of the separator to decrease. To counteract this decrease in capacity and to improve phase separation, it is possible to heat the oil for instance in a plate heat exchanger to a temperature not exceeding for example 90° C. before feeding the oil to the separator. This heating step improves the performance of the separator and reduces the residual oil content of the one or more other, non-oily phases but has the disadvantage that it inactivates part of the enzymes present and thereby increases the fresh enzyme requirements.

On the other hand, during the water degumming process, the presence of a larger amount of oil in the gums than would normally be considered acceptable now becomes fully acceptable since the oil is recuperated by the process according to the invention and besides, this extra amount of oil reduces the viscosity of the gums and thereby facilitates the dispersion of fresh enzymes if their addition is deemed to be desirable. Normally, this addition will not be necessary since fresh enzymes have already been added to the water used in the degumming and/or in crude oil but there may be occasions where an extra addition of fresh enzymes is considered to be worthwhile. Moreover, allowing the gums to contain more oil than normally increases the capacity of the separator used to isolate the gums from the oil.

In another embodiment of the process according to the invention, the triglyceride oil content of the gums is increased whereby the viscosity of the gums is reduced, by mixing triglyceride oil into the gums. Adjusting the pH of the gums can facilitate this mixing operation. This is especially true for gums originating from the acid refining process so when these gums are mixed with gums originating from a water degumming process, pH adjustment to lower their viscosity constitutes a preferred embodiment.

If enzymes with phospholipase activity are then mixed into the gum/oil mixture, they have been found to be far better dispersed than when the oil content of the gums has not been increased by the process according to the invention. The improvement is clearly demonstrated by the decrease in the period of time it takes for a certain amount of oil to float to the top of the gums/oil mixture. The total amount of oil liberated is of course larger when oil has been mixed into the gums but this mixing does not affect the residual oil content of the one or more phases from which the oily layer has been separated.

The oil to be mixed into the gums in said embodiment can be part of the oil recuperated but because the phospholipids content of the oil is immaterial in this application, degummed oil or crude oil that has not been degummed serves the purpose equally well. In the latter two cases, the diacylglycerol content in the oily layer will be lower than when the recuperated oil is recycled. Normally, the recuperated oily layer will be mixed with the water degummed oil and be sold as such or further processed. The free fatty acid content of the oily layer will be close to that of the crude oil if one or more enzymes with phospholipase C activity are used in the process according to the invention, so adding the oily layer to the crude oil does not increase the free fatty acid content of the latter. If enzymes with phospholipase A or B activity are used, the recuperated oil will have a higher free fatty acid content than the crude oil and mixing the recuperated oil with the crude oil may bring this outside specification and/or make it subject to price penalties.

The oil to be mixed into the gums in said embodiment can also be a fatty acid distillate (FAD) originating from a deodorisation operation. Obviously addition of FAD to gums will not increase the pH of the mixture but it has been observed that the viscosity of gums can be reduced by the presence of FAD. This option is preferably chosen if the recuperation of a fatty stream enriched with FFA is the object of the deoiling process.

The increase of the oil content of the gums is preferably controlled so as to maintain the gum viscosity at a set level, which level is equipment dependent. Small amounts of oil usually already reduce the viscosity of the gums quite markedly and once the viscosity has been reduced below a certain value, further addition of oil has hardly any further effect. In general, the amount of oil should be such as to increase the triglyceride oil content of the dry matter from some 35% by weight to at least 50% by weight, preferably at least 60% by weight and particularly preferably 100% by weight. Subsequent to the oil addition, some water may also be added to the mixture to facilitate phase separation.

In a continuous process, the use of dosing pumps and a static mixer to control the viscosity of the gum/oil mixture has been found to meet all technical requirements. Besides, such a mixer is easy to install and requires little or no maintenance, but this invention is not limited to this type of equipment. In batch processes, simultaneous addition of oils and gums into the batch vessel under agitation is preferred. The agitation is then continued until the mixture has a uniform appearance. The free enzyme can be added before or after mixing the oil and the gums and agitation is continued for a period of time that is very much equipment dependent. After the enzyme has been dispersed and hydrolysis has taken place, the agitation can be halted to permit the oil layer to rise to the top. Each step of a continuous process or a batch process as just described can be executed within the most suitable temperature range. For example, a first temperature range can be chosen in order to facilitate the dispersion of the enzymes into the gums, a second particular temperature range can be selected to facilitate the gums hydrolysis and a third temperature range can be selected to facilitate the phase separation.

When the oil has risen to the top, it can be separated by decantation but because it provides a sharper separation, the use of a centrifugal separator for the recuperation of the oily phase is preferred. To further improve the separation and thereby increase the oil yield and reduce the residual oil content of the other one or more phases, the mixture fed to the centrifugal separator can be heated to a temperature of at the most 90° C. while using for instance a plate heat exchanger but this heating has the disadvantage that it will inevitably inactivate at least part of the enzymes present and thus increase the fresh enzyme requirements.

Gums originating from the water degumming process are not the only type of gums that can profit from the process according to the invention. Gums originating from the acid degumming process and especially the acid refining process can also be profitable treated by process according to the invention. As disclosed in U.S. Pat. No. 4,927,544, gums resulting from the acid refining process can be very viscous. They can be so viscous that two centrifugal separators are needed to remove them from the acid refined oil. In a first stage the oil containing a separate gum phase is subjected to centrifugal separation in a first centrifugal separator to yield gums with low oil content and an oil that still contains a fraction of the gums originally present in the feed, in a second stage the oil obtained from the first stage is subjected to centrifugal separation in a second centrifugal separator to yield oil with a further reduced residual gum content. The process according to the invention simplifies the process disclosed in U.S. Pat. No. 4,927,544 by requiring only a single centrifugal separator since the oil present in the gums need no longer be lost by being recuperated.

Both the acid degumming process and the acid refining process comprise a stage in which a strong acid is allowed to react with the oil to be degummed and this acidity may cause some enzyme inactivation. Therefore, the addition of the enzyme is preferably postponed until the pH of the aqueous phase in the degumming process is raised by the addition of water in the acid degumming process or the addition of diluted caustic in the acid refining process respectively.

When enzymes with phospholipase A1, A2, B or C activity are mixed into gums, they have been found to be far better dispersed when the acidity of the gums has been decreased with an aqueous solution of, for example, sodium hydroxide. Good results have been obtained when the water phase subsequently separated from the gums exhibits a pH in the range of 5 to 10 or preferably in the range of 6 to 9. It seems that the reduction of the acidity has a direct influence on the viscosity of the gums. The pH of the gums is preferably adjusted just before at least part of the one or more enzymes with phospholipase activity is mixed into said gums. The pH adjustment can also enhance the activity of the enzymes used in the deoiling process. The pH adjustment can also facilitate the phase separation of the gums being deoiled. Therefore, the sequence comprising a first pH adjustment before at least part of the one or more enzymes with phospholipase activity is mixed into said gums, and/or a second pH adjustment after at least part of the one or more of said enzymes is mixed into said gums in order to maximise the activity of said enzymes and/or a third pH adjustment of the deoiled gums just before the phase separation falls within the scope of the invention.

Acylglycerols can be recuperated from gums resulting from the acid degumming process or the acid refining process by the process according to the invention by treating these gums as such or after mixing said gums with gums resulting from the water degumming process and/or after pH adjustment. If this treatment comprises the use of one or more enzymes with phospholipase A1, A2 and/or B activity, the recuperated oil will have an increased content of free fatty acids. On the other hand, if this treatment comprises the use of one or more enzymes with phospholipase C activity, the recuperated oil will have an increased content of diacylglycerols.

If an enzymatic degumming process employing phospholipase A1, A2 or B is used to treat the water degummed oil, the resulting gums are likely to contain only small amounts of triglyceride oil. Recuperating this oil is often not justified economically and disposing of the gum phase via the meal is therefore most advisable. However, recuperating this oil by the process according to the invention falls within its scope.

A remarkable advantage of gums obtained by the acid degumming or the acid refining process is that the non-hydratable phospholipids are hydrated and can therefore be hydrolysed by the one or more enzymes with phospholipase C activity. Therefore the maximum quantity of acylglycerols is recovered.

Figure 1:
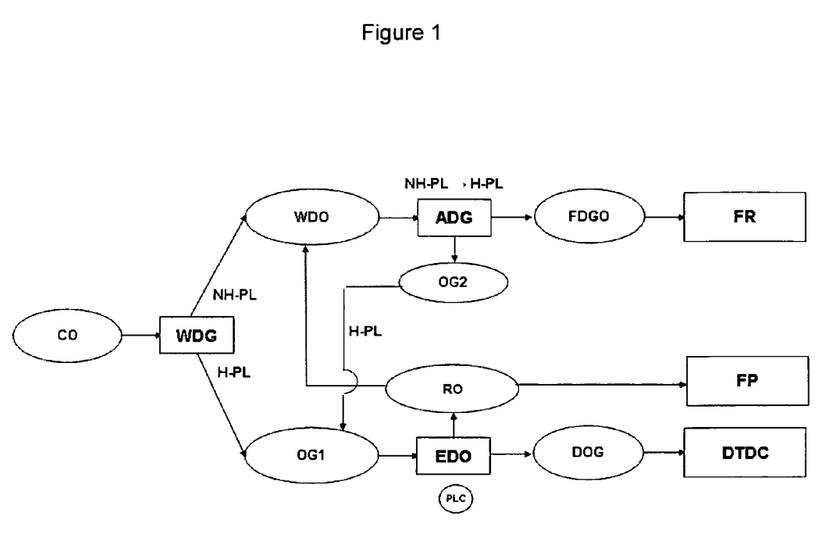
FIGS. 1 to 3 illustrate that a major feature of the process according to our invention is the possibility to install, the improved oil recuperation process according to our invention into existing oil mills with only limited retrofitting engineering.

FIG. 1 describes how the process according to our invention can be fitted into a typical oil mill comprising means for water degumming of crude oil and means for acid degumming of the water degummed oil. In FIG. 1 crude oil (CO) is water degummed (WDG), thereby providing oily gums (OG1) containing hydratable phospholipids (H-PL) and water degummed oil (WDO) containing non-hydratable phospholipids (NH-PL). The oily gums (OG1) originating from the water degumming process are treated by an enzymatic deoiling process (EDO) using enzymes with phospholipase C activity (PLC) providing recovered oil (RO) and de-oiled gums (DOG). The water degummed oil (WDO) originating from the water degumming process is subjected to an acid degumming process (ADG) employing citric acid for example. In this process the non-hydratable phospholipids are transformed into hydrated phospholipids to yield oily gums (OG2), which can be added to the oily gums (OG1) originating from the water degumming process (WDG) to be further deoiled. The fully degummed oil (FDGO) is then subjected to further refining (FR), typically bleaching and deodorisation. The deoiled gums (DOG) are typically included in the feed of a meal conditioning apparatus such as for example a desolventiser toaster dryer cooler (DTDC). Optionally, the recovered oil (RO), which is enriched in diacylglycerols can be processed separately (FP) and sold as speciality oil. In this case the recovered oil (RO) is not recycled by blending it with the water degummed oil (WDO). The option illustrated in FIG. 1 has the advantage that the recovered oil is enriched in diacylglycerols and not enriched in FFA.

Figure 2:
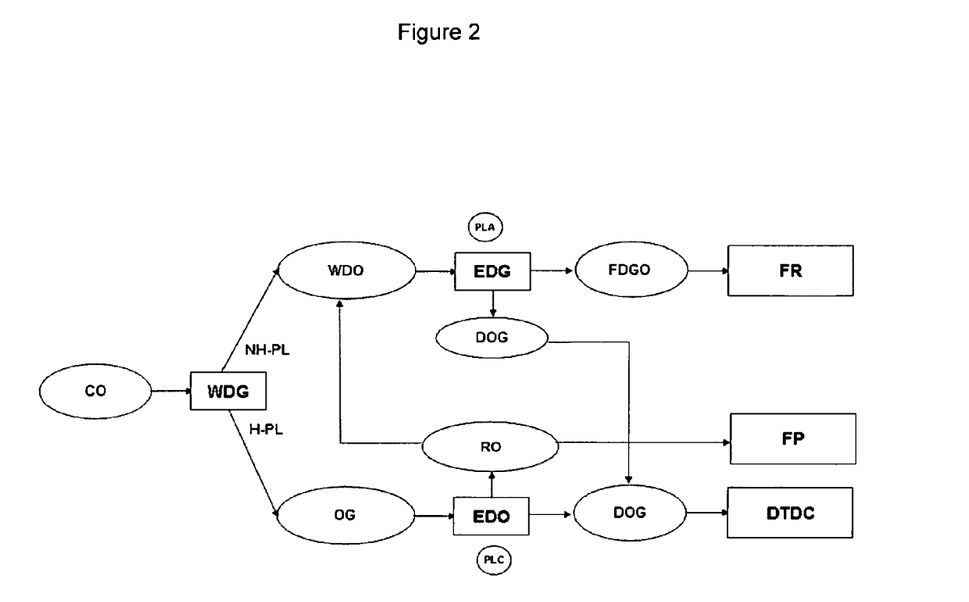

FIG. 2 describes how the process according to our invention can be fitted into a typical oil mill comprising means for water degumming of crude oil and means for the enzymatic degumming of the water degummed oil. In FIG. 2 crude oil (CO) is water degummed (WDG), thereby providing oily gums (OG) containing hydratable phospholipids (H-PL) and water degummed oil (WDO) containing non-hydratable phospholipids (NH-PL). The oily gums (OG) originating from the water degumming are treated by an enzymatic deoiling (EDO) process using enzymes with phospholipase C activity (PLC) providing recovered oil (RO) and de-oiled gums (DOG). The water degummed oil (WDO) originating from the water degumming process is subjected to an enzymatic degumming process (EDG) employing enzymes with phospholipase A1 and/or A2 (PLA) activity. The fully degummed oil (FDG) is then subjected to further refining (FR), typically bleaching and deodorisation. The deoiled gums (DOG) are typically included in the feed of a DTDC. Optionally, the recovered oil (RO), which is enriched in diacylglycerols can be processed separately and sold as speciality oil. In this case the recovered oil (RO) is not recycled by blending it with the water degummed oil (WDO).

Figure 3:
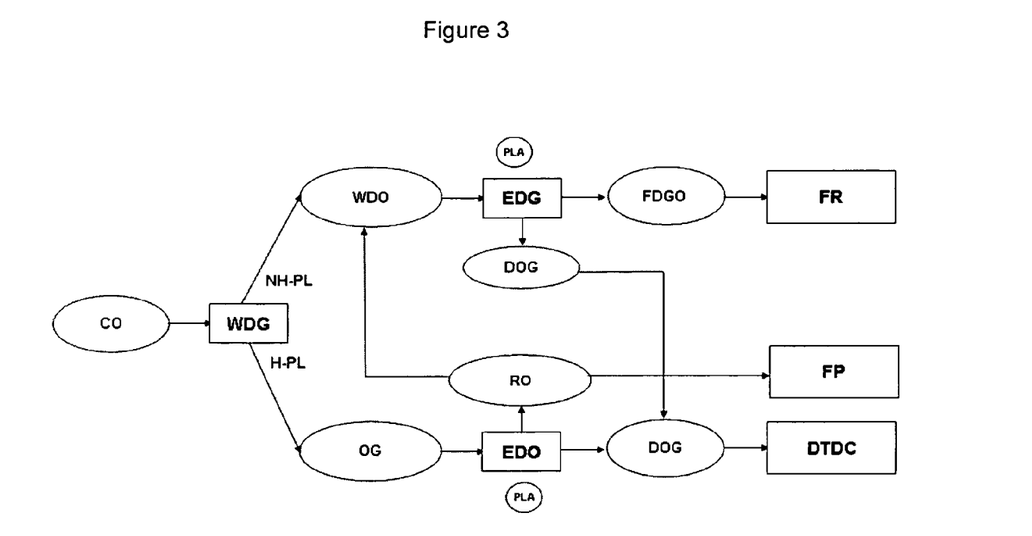

Alternatively the enzymatic oil recuperation process (EDO) can employ enzymes with phospholipase A activity (PLA) providing recovered oil (RO) enriched in FFA. This alternative is illustrated in FIG. 3. The option illustrated in FIG. 3 is preferred if oil a stream enriched in FFA is aimed for.

The invention claimed is:

1. A process for the recuperation of acylglycerols or acylglycerols containing free fatty acids from gums, present as aqueous emulsions, said gums being obtained by subjecting triglyceride oil to one or more degumming processes, said recuperation process comprising the steps of: subjecting said gums to enzymatic hydrolysis catalysed by one or more enzymes with phospholipase activity; allowing said gums to separate into two or more phases, said two or more phases including at least an oily phase and an aqueous phase; and recuperating said oily phase comprising acylglycerols or acylglycerols containing free fatty acids; wherein said enzymatic hydrolysis is accelerated by adding at least part of the one or more enzymes with phospholipase activity to at least part of the water used in the recuperation and/or at least one degumming process, and/or at least part of said triglyceride oils treated in said degumming process, and/or by facilitating mixing at least part of said one or more enzymes with phospholipase activity into said gums by increasing the triglyceride oil content of said gums wherein said one or more degumming process is an acid degumming process.

2. The process according to claim 1 in which at least some of the phospholipase present in said aqueous phase is also recuperated as an aqueous solution and used at least partially in said acid degumming process by adding it to the oil being acid degummed after the degumming acid has been diluted with water.

3. The process according to claim 1 in which the pH of the gums resulting from said acid degumming process is adjusted to a value in the range of 5 to 10 and preferably 6 to 9 before at least part of the one or more enzymes with phospholipase activity is mixed into said gums.

4. A process for the recuperation of acylglycerols or acylglycerols containing free fatty acids from gums, present as aqueous emulsions, said gums being obtained by subjecting triglyceride oil to one or more degumming processes, said recuperation process comprising the steps of: subjecting said gums to enzymatic hydrolysis catalysed by one or more enzymes with phospholipase activity; allowing said gums to separate into two or more phases, said two or more phases including at least an oily phase and an aqueous phase; and recuperating said oily phase comprising acylglycerols or acylglycerols containing free fatty acids; wherein said enzymatic hydrolysis is accelerated by adding at least part of the one or more enzymes with phospholipase activity to at least part of the water used in the recuperation and/or at least one degumming process, and/or at least part of said triglyceride oils treated in said degumming process, and/or by facilitating mixing at least part of said one or more enzymes with phospholipase activity into said gums by increasing the triglyceride oil content of said gums wherein said one or more degumming process is an acid refining process.

5. The process according to claim 4 in which at least some of the phospholipase present in said aqueous phase is also recuperated as an aqueous solution and used at least partially in said acid refining process by adding it to the oil being acid refined after the degumming acid has been partially neutralised with diluted caustic.

6. The process according to claim 4 in which the pH of the gums resulting from said acid refining process is adjusted to a value in the range of 5 to 10 and preferably in the range of 6 to 9 before at least part of the one or more enzymes with phospholipase activity is mixed into said gums.

7. A process for the recuperation of acylglycerols or acylglycerols containing free fatty acids from gums, present as aqueous emulsions, said gums being obtained by subjecting triglyceride oil to one or more degumming processes, said recuperation process comprising the steps of: subjecting said gums to enzymatic hydrolysis catalysed by one or more enzymes with phospholipase activity; allowing said gums to separate into two or more phases, said two or more phases including at least an oily phase and an aqueous phase; and recuperating said oily phase comprising acylglycerols or acylglycerols containing free fatty acids; wherein said enzymatic hydrolysis is accelerated by adding at least part of the one or more enzymes with phospholipase activity to at least part of the water used in the recuperation and/or at least one degumming process, and/or at least part of said triglyceride oils treated in said degumming process, and/or by facilitating mixing at least part of said one or more enzymes with phospholipase activity into said gums by increasing the triglyceride oil content of said gums wherein said one or more enzymes with phospholipase activity exhibit phospholipase C activity.

8. The process according to claim 1 in which the separator used in said acid degumming process is adjusted or only a single separator is used so that the oil content of said gums is increased and fresh enzyme with phospholipase activity is dispersed in the mixture.

9. The process according to claim 3 in which a single separator is used in said acid refining process so that the oil content of said gums is increased and fresh enzyme with phospholipase activity is dispersed in the mixture.

* * * * *